United States Patent
Kai et al.

(10) Patent No.: US 6,891,936 B2
(45) Date of Patent: May 10, 2005

(54) REMOTE DATA CONTROL SYSTEM AND MEASURING DATA GATHERING METHOD

(75) Inventors: Akinori Kai, Kyoto (JP); Masanao Kawatahara, Kyoto (JP); Toshihiko Harada, Kyoto (JP)

(73) Assignee: Arkray, Inc., Kyoto (JP)

(*) Notice: Subject to any disclaimer, the term of this patent is extended or adjusted under 35 U.S.C. 154(b) by 0 days.

(21) Appl. No.: 10/296,871

(22) PCT Filed: May 30, 2001

(86) PCT No.: PCT/JP01/04579
§ 371 (c)(1),
(2), (4) Date: Nov. 27, 2002

(87) PCT Pub. No.: WO01/93557
PCT Pub. Date: Dec. 6, 2001

(65) Prior Publication Data
US 2003/0147515 A1 Aug. 7, 2003

(30) Foreign Application Priority Data
May 31, 2000 (JP) ........................................ 2000-163109

(51) Int. Cl.⁷ ............................................ H04M 11/00
(52) U.S. Cl. ............................ 379/106.02; 379/106.01; 128/904
(58) Field of Search .............. 379/106.02, 93.05–93.08, 379/106.01, 90.01; 128/903, 904, 715

(56) References Cited

U.S. PATENT DOCUMENTS 5,226,431 A   7/1993   Bible et al.
5,367,555 A * 11/1994  Isoyama ...................... 379/38
6,402,691 B1 * 6/2002  Peddicord et al. ..... 379/106.02

FOREIGN PATENT DOCUMENTS

| JP | 2-279056    | 11/1990 |
| JP | 9-253058    | 9/1997  |
| JP | 10-33487    | 10/1998 |
| JP | 11-47101    | 2/1999  |
| JP | 11-206716   | 3/1999  |
| JP | 11-122369   | 4/1999  |
| JP | 2000-139857 | 5/2000  |

* cited by examiner

Primary Examiner—Wing F. Chan
(74) Attorney, Agent, or Firm—Merchant & Gould P.C.

(57) ABSTRACT

It is an object of the present invention to provide a remote data management system with which, by keeping the transmission of measured data from measurers from being concentrated at particular times, the measured data can be gathered efficiently and the party managing the data can suffice with a minimal equipment investment. In patient households (B, C . . . ), a personal measuring device (3) is connected to a communications device (2) via a cable or the like, and data that are measured by the personal measuring device (3) are transferred to the communications device (2) and stored. A server (1) of a medical institution (A) sends a data transmission request to the communications device (2) in each patient's household via a public communications network 10 daily, biweekly, or monthly, for example. When the communications device (2) receives the data transmission request it transmits the stored measured data to the server (1).

22 Claims, 8 Drawing Sheets

REMOTE DATA CONTROL SYSTEM AND MEASURING DATA GATHERING METHOD

TECHNICAL FIELD

The present invention relates to remote data management systems, such as remote health management systems for remotely managing patient health, in which patients outside of medical institutions use personal measuring devices to measure various personal data and transmit the measured data to medical institutions or the like via a public communications network.

BACKGROUND ART

Conventionally, personal measuring devices (e.g. electrocardiographs, sphygmomanometers, blood glucose meters, and urine analysis devices) are known with which a patient can measure various personal data outside of medical institutions.

For example, diabetics, who must regulate their blood glucose level daily, use such a personal measuring device (blood glucose meter) to measure their blood glucose level four times a day (before or after breakfast, lunch, and dinner, and before going to sleep), and record the results of those measurements in a medical records book, for example. Then, upon visiting a hospital once a month or after longer intervals, patients present their physician with measurements recorded up to that date and are advised regarding management of their blood glucose level.

However, there have been problems with patients living in remote areas having difficulties visiting the hospital, and with an approach where patients are responsible for recording the measured data, there is the problem of patients forgetting to record measured data. Accordingly, systems are known in which personal measuring devices are capable of connecting to the server of medical institutions or the like via public communications networks, such as telephone networks, and each time a patient performs a measurement, the measured data are transmitted to the server from the personal measuring device, so that accurate measured data can be gathered at the medical institution and patients can be diagnosed and receive lifestyle guidance from their physicians while at home.

With the above conventional system, however, because the times at which patients take measurements and transmit measured data are concentrated at certain times of the day, there was the problem of the server being difficult to access at those times. To solve this problem, solutions such as increasing equipment for connecting to the server from the outside are necessary, which for medical institutions leads to the problem of an increased equipment investment. An additional problem with this conventional system was that it required patients to spend time transmitting data after each measurement and bear the communications costs.

In order to solve the foregoing problems, it is an object of the present invention to supply a remote data management system with which measured data can be efficiently gathered, by keeping the transmission of measured data transmitted by measurers from being concentrated at certain periods of the day, and with which equipment investment can be minimized.

DISCLOSURE OF INVENTION

To achieve the above objects, a remote data management system of the present invention includes a measuring device with which a managed person can perform a measurement of data and a data management device for managing measured data for each managed person obtained by the measuring device. The measured data obtained with the measuring device are collected in and managed by the data management device via a communications network. The remote data management system includes a communications device to which managed persons connect their measuring device so as to use it, having a measured data storage means for storing measured data obtained by the measuring device and a data transmission means for transmitting the measured data over the communications network. When connected to the measuring device, the communications device receives measured data from the measuring device and stores the measured data in the measured data storage means, and when a transmission request for the measured data is received from the data management device, the communications device reads out the measured data stored in the measured data storage means and transmits the measured data to the data management device via the communications network using the data transmission means, and is provided with a control means for controlling the timing at which the data management device connects to the communications device of each managed person via the communications network and performs a transmission request for the measured data.

Thus, the control means of the data management device adjusts the timing at which the transmission requests are sent to the transmission device of each managed person, so that the transmission of measured data from managed persons can be spread out so that it is not concentrated at particular times. Also, the measured data are stored in the communications device, so that if the frequency of the transmission requests is adjusted suitably, a plurality of measured data can be aggregated and received at once. Accordingly, a remote data management system with which the measured data of managed persons can be gathered efficiently and a minimum equipment investment is required can be provided.

It should be noted that managed persons include patients and other individuals requiring their health to be monitored by a medical institution due to a history of illness or for other reasons. The communications network includes dedicated lines and public communications networks such as CATV networks and telephone networks.

In the remote data management system, it is preferable that the data management device includes a received data storage means for storing received measured data together with a time of reception for each managed person, and that the control means determines the timing at which to carry out the transmission request to the communications device of each managed person based on a most recent time of reception of the measured data stored in the received data storage means for that managed person.

Thus, if the transmission request is performed after a predetermined amount of time has passed from the time at which measured data were previously received from a particular managed person, then the measured data of each managed person can be gathered at a set interval.

In the remote data management system, it is preferable that the data management device includes a data processing means for analyzing received measured data, and that the results of analysis by the data processing means are transmitted to the communications device. Thus, if, for example, the measured data are outside of a normal range, then that managed person can be notified or instructed to visit the medical institution and be examined directly by his physician.

In the remote data management system, it is preferable that the data processing means creates a message for alerting a managed person to perform periodic measurements and includes the message in the results of the analysis, when a number of measured data sets that are measured after previous measured data of that managed person are received is less than a number of measurements that should have been performed. Thus, if a managed person misses a measurement even though periodic measurements are required, this can be detected and the managed person can be alerted.

In the remote data management system, it is preferable that when the communications device receives the data transmission request from the data management device, the communications device retrieves from the measured data that are stored in the measured data storage means measured data that have not yet been transmitted to the data management device, and transmits them to the data management device. Thus, the amount of transmitted data can be reduced, so that transmission times can be shortened and data management on the data management device becomes easy.

In the remote data management system, it is preferable that the communications network is a telephone network and that the communications device is a mobile communications type telephony device. It should be noted that the mobile communications type telephone device includes a portable telephone and a PHS(Personal Handyphone System). Thus, the managed person can take measurements and transmit measured data from any location.

In the remote data management system, it is preferable that the measuring device is a blood glucose level meter. Thus, the blood glucose level readings before or after meals and before going to sleep of diabetic patients for whom self monitoring of blood glucose (SMBG) is necessary can be aggregated in the data management device via a communications network and managed, so that the effort conventionally required to record the measured results in a medical records book is unnecessary and thus the burden on patients can be reduced. Also, accurate measured data can be received.

In order to achieve the above objects, a measurement system of the present invention has a measuring device with which a managed person measures data, and via a communications network, the measured data obtained by the measuring device is transmitted to a data management device for managing the measured data of the managed person, and includes a communications device having a measured data storage means for storing measured data obtained with the measuring device and a data transmission means for transmitting the measured data over the communications network. When connected to the measuring device, the communications device receives measured data from the measuring device and stores the measured data in the measured data storage means, and when a transmission request for the measured data is received from the data management device, the communications device reads out the measured data stored in the measured data storage means and transmits the measured data to the data management device over the communications network using the data transmission means.

Thus, data that are measured by managed persons are stored in the measured data storage means of the communications device, and when there is a transmission request from the data management device, the stored measured data are read out and transmitted, so that the timing at which data are transmitted from the communications device of each managed person can be controlled at the data management device side, and in contrast to the conventional approach of transmitting data each time a measurement is performed by the managed persons, the transmission of data to the data management device can be kept from being concentrated at particular times. Also, if the frequency of the transmission requests is adjusted suitably, a plurality of measured data readings can be aggregated and sent together, which improves transmission efficiency. Consequently, a management system with which the measured data of managed persons can be efficiently gathered in the data management device and with which the equipment investment on the data management device side is small can be provided.

In the measurement system, it is preferable that when the communications device receives the transmission request for the measured data from the data management device, the communications device retrieves, from the measured data that are stored in the measured data storage means, only measured data that have not yet been transmitted to the data management device, and transmits them to the data management device using the data transmission means. Thus, the data transmission amount can be reduced and the transmission time can be shortened.

In the measurement system, it is preferable that the communications network is a telephone network and that the communications device is a mobile communications type telephony device. It should be noted that examples of the mobile communications type telephone device include a portable telephone and a PHS. Thus, the managed person can take measurements and transmit measured data from any location.

In the measurement system, it is preferable that the measuring device is a blood glucose level meter. Thus, the blood glucose level readings before or after meals and before going to sleep of diabetic patients for whom self monitoring of blood glucose (SMBG) is necessary can be aggregated in the data management device via a communications network and managed, so that the effort conventionally required to record the measured results in a medical records book is unnecessary and thus the burden on patients can be reduced. Also, accurate measured data can be received.

To achieve the above objects, a communications device of the present invention is a communications device in a remote data management system including a measuring device with which managed persons can perform a measurement of data and a data management device for managing measured data for managed persons obtained with the measuring device, wherein the communications device is used by managed persons by connecting it to the measuring device, and is connected to the data management device via a communications network and transmits measured data that are received from the measuring device to the data management device. The communications device has a measured data storage means for storing measured data obtained with the measuring device and a data transmission means for transmitting the measured data over the communications network. When connected to the measuring device, the communications device receives measured data from the measuring device and stores the measured data in the measured data storage means, and when a transmission request for the measured data is received from the data management device, the communications device reads out the measured data stored in the measured data storage means and transmits the measured data to the data management device over the communications network using the data transmission means.

Thus, data that are measured by managed persons are stored in the measured data storage means, and when there is a transmission request from the data management device, the stored measured data are read out and transmitted, so that the timing at which data are transmitted from the communications device of each managed person can be controlled at the data management device side. In contrast to the conventional approach of transmitting data each time a measurement is performed by the managed persons, the transmission of data to the data management device can be kept from being concentrated at particular times. Also, if the frequency of the transmission requests is suitably adjusted, a plurality of measured data readings can be aggregated and sent together, which improves transmission efficiency. Consequently, a communications device with which the measured data of managed persons can be efficiently collected in the data management device and with which the equipment investment on the data management device side is small can be provided.

In the communications device, it is preferable that when the communications device receives the transmission request for the measured data from the data management device, the communications device retrieves, from the measured data that are stored in the measured data storage means, measured data that have not yet been transmitted to the data management device, and transmits them to the data management device using the data transmission means. Thus, the data transmission amount can be reduced and transmission times can be shortened.

In the communications device, it is preferable that the communications network is a telephone network and can be configured as a mobile communications type telephony device. It should be noted that examples of the mobile communications type telephone device include a portable telephone and a PHS. Thus, the managed person can take measurements and transmit measured data from any location.

To achieve the foregoing objects, a data management device of the present invention is a data management device that receives via a communications network measured data from a measurement system including a measuring means with which managed persons can perform a measurement of data, a measured data storage means for storing the measured data obtained by the measuring means, and a data transmission means for reading out the measured data from the measured data storage means when a transmission request for the measured data is received via a communications network, and manages the measured data. The data management device includes a control means that is connected to the measuring system of each managed person via the communications network and controls the timing at which the transmission request for the measured data is performed.

Thus, the timing at which the measured data of managed persons are transmitted from the management system to the data management device is controlled at the data management device side, so that in contrast to the conventional approach of transmitting data each time a measurement is performed by managed persons, the transmission of data to the data management device can be kept from being concentrated at particular times. Also, if the frequency of the transmission requests is adjusted suitably, a plurality of measured data readings can be aggregated and sent together, which improves transmission efficiency. Consequently, it is possible to provide a data management device with which the measured data of managed persons can be efficiently collected and with which the investment toward equipment, for example, required for connecting to the outside is kept small.

In the data management device, it is preferable that a received data storage means for storing measured data received from the measuring system together with a time of reception for each managed person further is provided, and that the control means determines the timing at which to carry out the transmission request to the measuring system of each managed person based on a most recent time of reception of the measured data stored in the received data storage means for that managed person.

Thus, if for example the transmission request is performed after a predetermined amount of time has passed from the time at which measured data were previously received from a particular managed person, then the measured data of each managed person can be gathered at a constant interval.

In the data management device, it is preferable that a data processing means for analyzing measured data that are received from the measuring system is provided, and that the data management device transmits results of the analysis by the data processing means to the measuring system using the communications means. Thus, if, for example, the measured data are outside of a normal range, then that managed person can be notified of this or instructed to visit the medical institution and be examined directly by his physician.

In the data management device, it is preferable that the data processing means incorporates into the results of the analysis a message alerting a managed person to perform periodic measurements, when, of the measured data that are received from the measuring system, the number of measured data sets that are measured after previously measured data of that managed person are received is less than a number of measurements that should have been performed. Thus, if a managed person misses a measurement even though periodic measurements are required, this can be detected and the managed person can be reminded.

To achieve the foregoing objects, a method for gathering measured data of the present invention is a method wherein, in a remote data management system including a measuring device with which managed persons can perform a measurement of data, a data management device for managing measured data of the managed persons obtained with the measuring device, and a communications device that is used by the managed persons by connecting it to the measuring device, has a measured data storage means for storing the measured data, and transmits the measured data to the data management device via a communications network, the measured data of each managed person obtained with the measuring device are gathered in the data management device. The measured data gathering method includes connecting the measuring device to the communications device and storing the measured data obtained with the measuring device to the measured data storage means of the communications device, connecting the data management device to the communications device of each managed person via the communications network and performing a transmission request for the measured data at a predetermined timing, and the communications device reading out the measured data from the measured data storage means and transmitting the measured data to the data management device via the communications network when the transmission request for the measured data is received from the data management device.

Thus, the timing at which the measured data of managed persons are transmitted from the management system to the data management device is controlled at the data management device side, so that in contrast to the conventional approach of transmitting data each time a measurement is performed by managed persons, the transmission of data to the data management device can be kept from being concentrated at particular times. Also, if the frequency of the transmission requests is adjusted suitably, a plurality of measured data readings can be aggregated and sent together, which improves transmission efficiency. Consequently, the measured data of managed persons can be efficiently collected and the investment toward equipment, for example required for connecting to the outside on the data management device side, is kept small.

In the measured data gathering method, it is preferable that the timing at which the data management device carries out the transmission request for measured data to the communications device of each managed person is determined based on the last time the measured data for that managed person was received. Thus, if for example the transmission request is performed after a predetermined amount of time has passed from the time at which measured data were last received from a particular managed person, then the measured data of each managed person can be gathered at a constant interval.

In the measured data gathering method, it is preferable that when the transmission request for the measured data is received from the data management device, measured data from among the measured data stored in the measured data storage means that have not yet been transmitted to the data management device are retrieved, and only the measured data that are retrieved are transmitted to the data management device. Thus, the amount of transmitted data can be reduced and transmission times can be shortened.

To achieve the foregoing objects, a first program storage medium of the present invention is a program storage medium on which is stored a program for controlling the operation of a communications device in a remote data management system that includes a measuring device with which managed persons can perform a measurement of data and a data management device for managing the measured data of each managed person that are obtained with the measuring device, wherein the communications device is used by the managed persons by connecting it to the memory device and is connected to the data management device via a communications network and transmits the measured data that are received from the measuring device to the data management device. The program executes on the communications device a storage process for receiving measured data from the measuring device and storing the measured data in a storage means and a transmission process for reading out the measured data stored in the storage means and transmitting the measured data to the data management device via the communications network when the transmission request for the measured data is received from the data management device.

With this storage medium, the stored program can be executed on a CPU or the like so as to achieve the communications device of the present invention.

To achieve the foregoing objects, a second program storage medium of the present invention is a program storage medium on which is stored a program for controlling operation of a data management device for gathering, and managing, measured data from each managed person via a communications network from a measuring system that includes a measuring means with which the managed persons can perform a measurement of data, a storage means for storing measured data obtained with the measuring means, and a data transmission means for reading out the measured data from the storage means and transmitting the measured data over the communications network when a transmission request for the measured data is received via the communications network. The program executes on the data management device a process for connecting to the measuring system of each managed person via the communications network and carrying out the transmission request for the measured data at a predetermined timing.

With this storage medium, the stored program can be executed on a CPU or the like so as to achieve the data management device of the present invention.

To achieve the foregoing objects, a third program storage medium of the present invention is a program storage medium on which is stored a program for controlling operation of a data management device that receives and manages measured data of managed persons via a communications network from a measurement system including a measuring means with which the managed persons can perform a measurement of data, a storage means for storing measured data obtained with the measuring means, and a data transmission means for reading out the measured data from the storage means and transmitting the measured data over the communications network when a request for transmission of the measured data is received via the communications network, wherein the data management device is provided with a received data storage means for storing the measured data of each managed person that are received and a time of reception thereof. The program executes on the data management device a procedure with which the data management device determines a timing at which the request for transmission of the measured data should be sent to the measuring system of each managed person based on a most recent time of reception of the measured data stored in the received data storage means for that managed person, and connects to the measuring system of each managed person via the communications network and performs the request for transmission of the measured data at the determined timing.

With this storage medium, the stored program can be executed on a CPU or the like so as to achieve the communications device of the present invention. It should be noted that for the first and third program storage media, it is possible to employ a ROM, a flexible disk, a hard disk, or any storage medium such as a CD-ROM that can be read by a computer.

BEST MODE FOR CARRYING OUT THE INVENTION

Hereinafter, an embodiment of the present invention is described in reference to the drawings.

Figure 1:
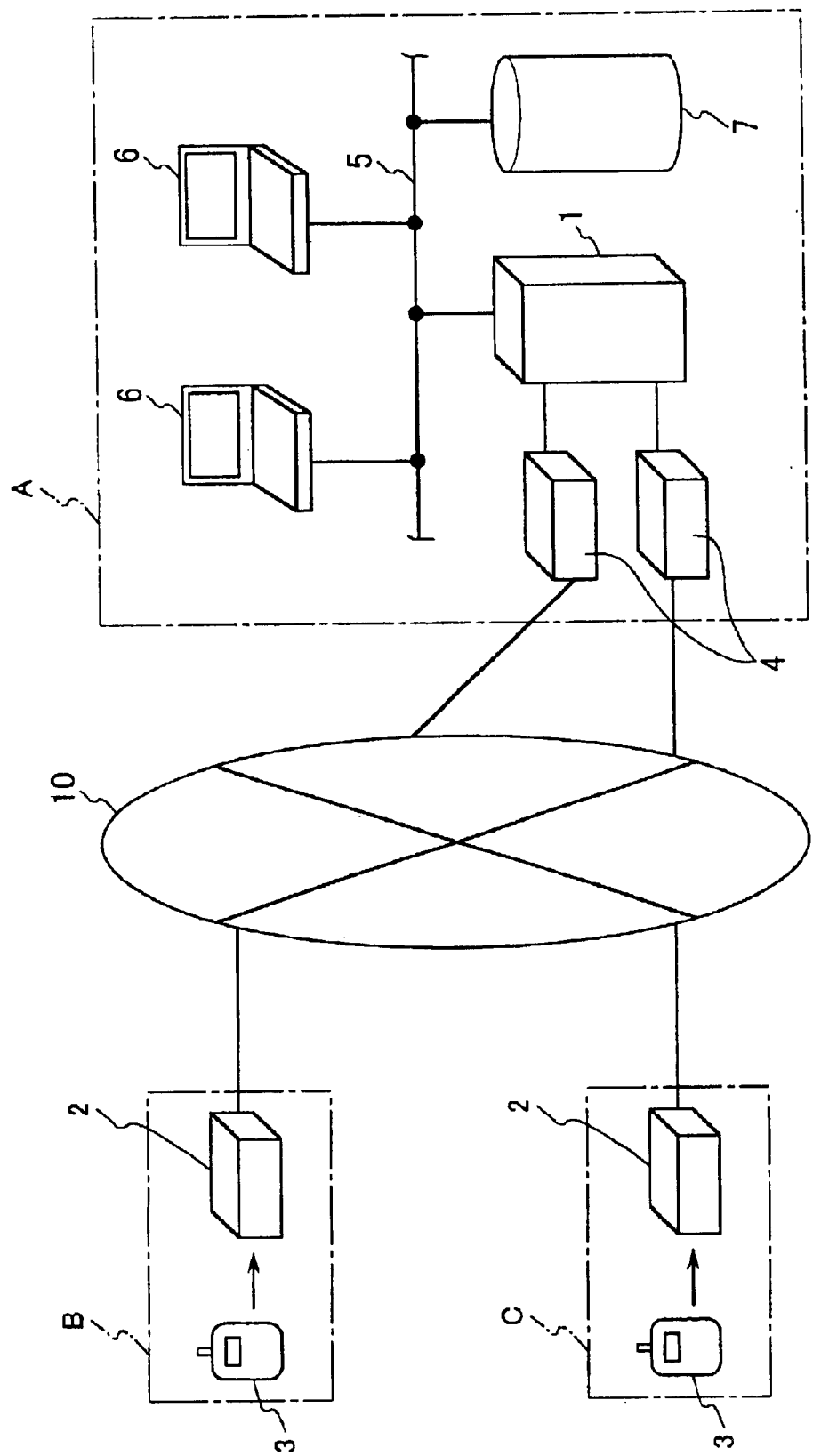
FIG. 1 is a block diagram showing the configuration of a remote health management system according to one embodiment of the present invention.

FIG. 1 is a block diagram schematically showing the configuration of a remote health management system (remote data management system) according to an embodiment of the present invention. As shown in FIG. 1, the remote health management system is configured so that a server 1 (data management device) of a medical institution A is connected to a communications device 2 in each household B, C, etc. of a patient (managed persons) via a modem 4 and a public communications network 10 such as a telephone network. The server 1 of the medical institution A is connected to computer terminals 6 and a memory device 7, for example, within the medical institution A via a LAN 5.

The communications device 2 in each patient household B, C, etc. is connected by cable or the like to a personal measuring device 3 with which a patient can measure data. The personal measuring device 3 and the communications device 2 together create a measuring system. Data measured using the personal measuring device 3 are obtained by the communications device 2 and stored therein.

Figure 2:
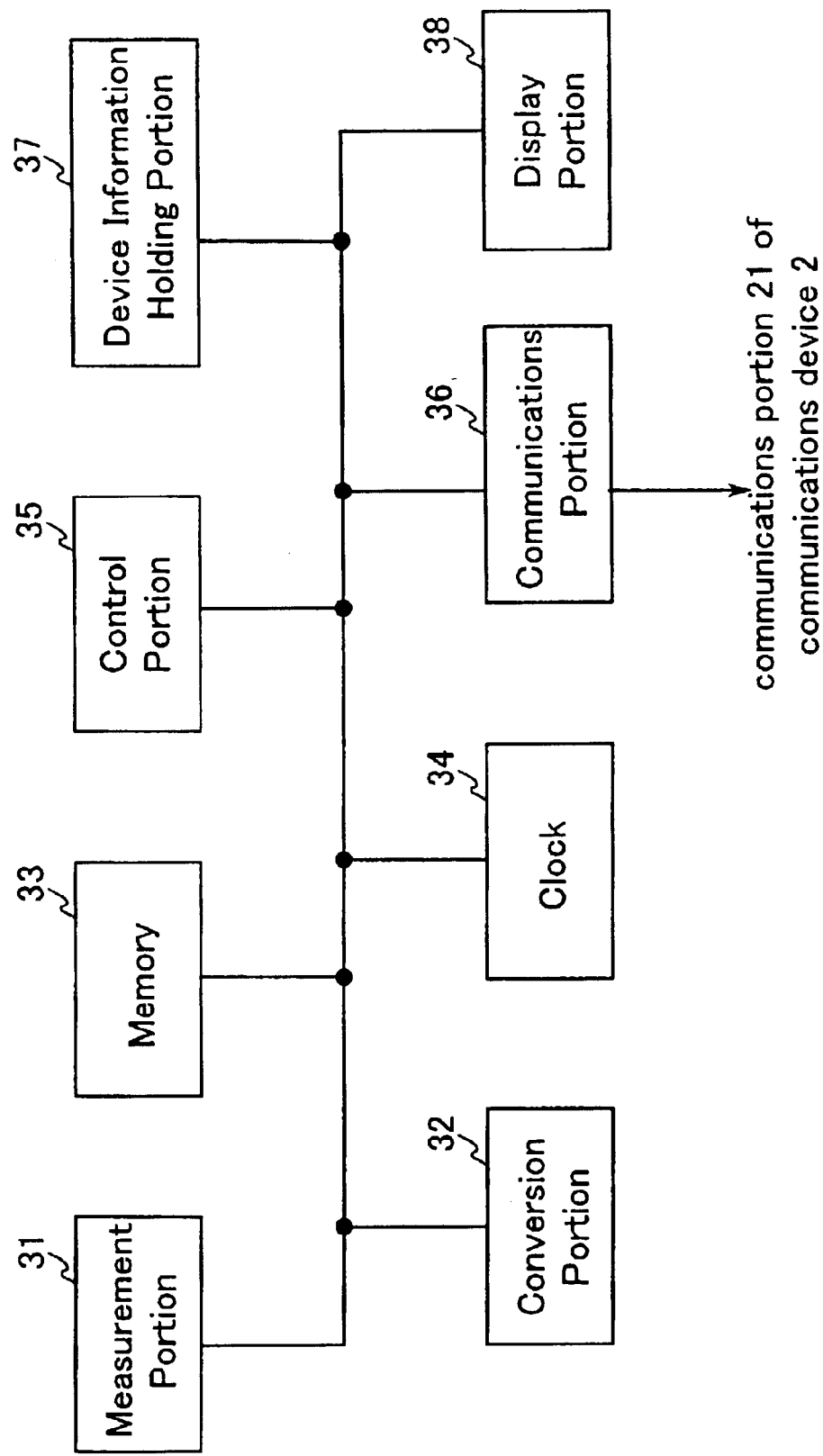
FIG. 2 is a block diagram showing the configuration of a personal measuring device used by patients in the remote health management system.

FIG. 2 is a block diagram showing the configuration of the personal measuring device 3. As shown in FIG. 2, the personal measuring device 3 includes a measurement portion 31, a conversion portion 32, a memory 33, a clock 34, a control portion 35, a communications portion 36, a device information holding portion 37, and a display portion 38.

The measurement portion 31 has a sensor that corresponds to the function of the personal measuring device 3, and measures data in accordance with a control by the control portion 35. For example, if the personal measuring device 3 is an electrocardiograph, then the electrodes that are brought into contact with the patient's chest and limbs serve as sensors, and the measuring portion 31 measures action potentials using these electrodes. Alternatively, if the personal measuring device 3 is a blood glucose level meter, then the measurement portion 31 is provided with sensors for electrically or optically measuring blood glucose levels from a test paper on which is placed a small amount of blood drawn from the patient's fingertip, for example. Of course, the personal measuring device 3 is not limited to only the electrocardiograph or blood glucose level meter mentioned above.

The conversion portion 32, in accordance with a control by the control portion 35, determines the concentration of a measured substance by executing a process such as IV conversion or AD conversion in response to information obtained by the measurement portion 31 (e.g. current value from electrodes or reflectance of test paper), and stores this information in the memory 33 as measured data. At this time, in correlation with the measured data, information on the time of data measurement is obtained from the clock 34 and stored in the memory 33.

The control portion 35 is made of a CPU, for example, and is operated in accordance with a program so as to control the operation of each portion of the personal measuring device 3. The communications portion 36 is connected via a cable or the like to a communications portion 21 of the communications device 2, and in accordance with a control of the control portion 35, transmits measured data or the like to the communications device 2. The display portion 38 has a liquid crystal display or the like, and displays messages or the like relating to operation commands, for example.

The device information holding portion 37 stores various kinds of information pertaining to that personal measuring device 3, and is achieved by a rewritable nonvolatile memory such as an EEPROM or a RAM for which backup power is provided. This information includes, for example, the unique device ID number that is allocated to each personal measuring device 3, the patient ID number of the patient in possession of that personal measuring device 3, and information pertaining to reagents used by the personal measuring device 3 (such as the measured items and the reagent lot number).

Figure 3:
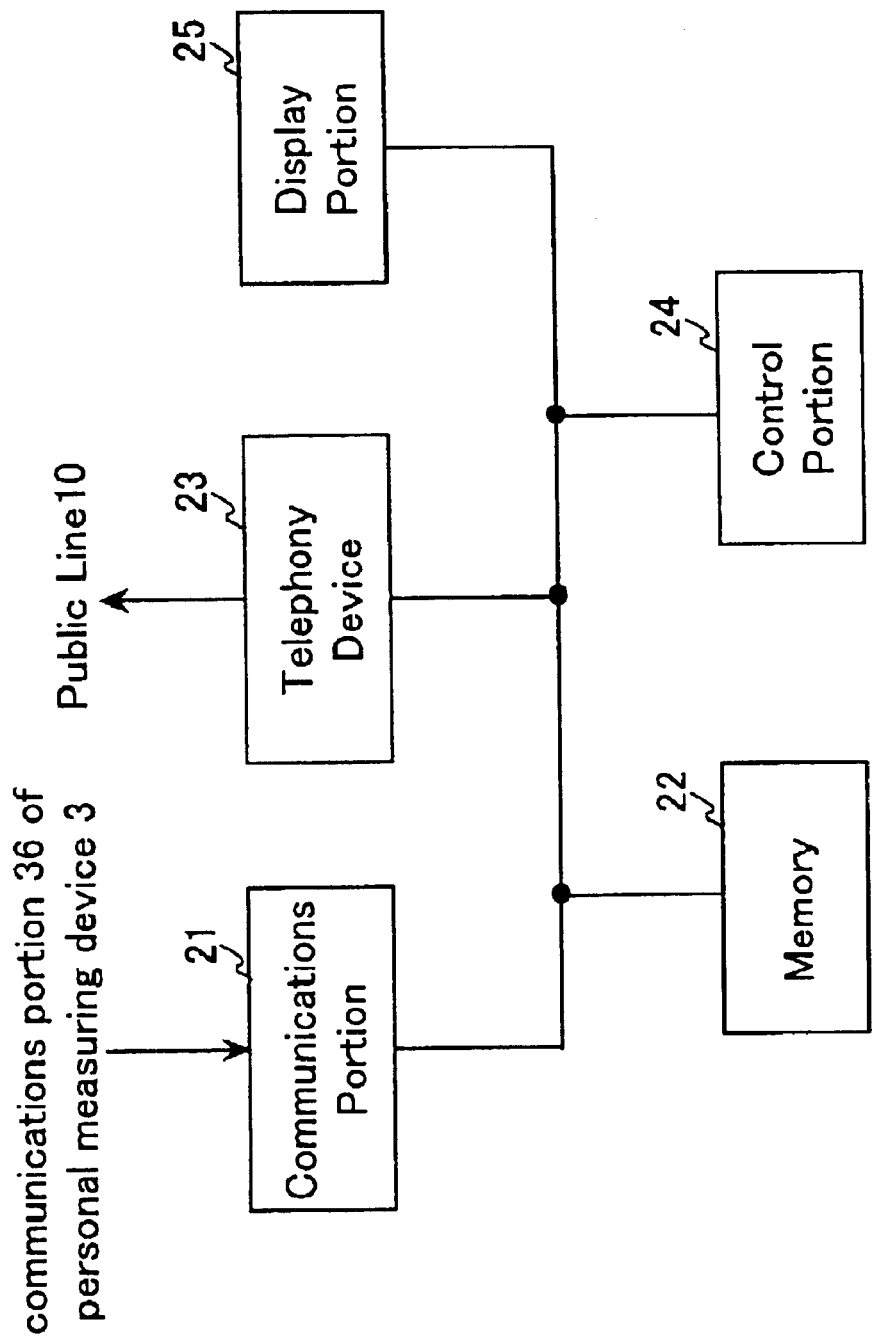
FIG. 3 is a block diagram showing the configuration of a communications device used by patients in the remote health management system.

FIG. 3 is a block diagram showing the configuration of a communications device 2. As shown in FIG. 3, each communications device 2 is provided with the communications portion 21, a memory 22 (measured data storage means), a telephony device 23 (data transmission means), a control portion 24, and a display portion 25.

The communications portion 21 is connected to the communications portion 36 of the personal measuring device 3, and receives measured data or the like from the personal measuring device 3. The memory 22 is for storing the measured data or the like received by the communications portion 21 from the personal measuring device 3, and can be achieved by a rewritable nonvolatile memory such as an EEPROM or a RAM for which a backup power source is provided. The telephony device 23 is connected to the public communications network 10 (telephone network), and sends and receives data, for example, to and from the server 1 of the medical institution A via the public communications network 10.

The control portion 24 is a CPU, for example, and operates in accordance with a program so as to control the operation of each portion of the communications device 2. The display portion 25 has a liquid crystal display, for example, and displays messages pertaining to operation commands and messages that are sent to the patient from the medical institution A.

The communications device 2 can be a device specifically for connecting to a telephone line at the patient's residence, or it can be achieved by incorporating the necessary memory and program into a mobile telephony device such as a portable telephone or a PHS.

Figure 4:
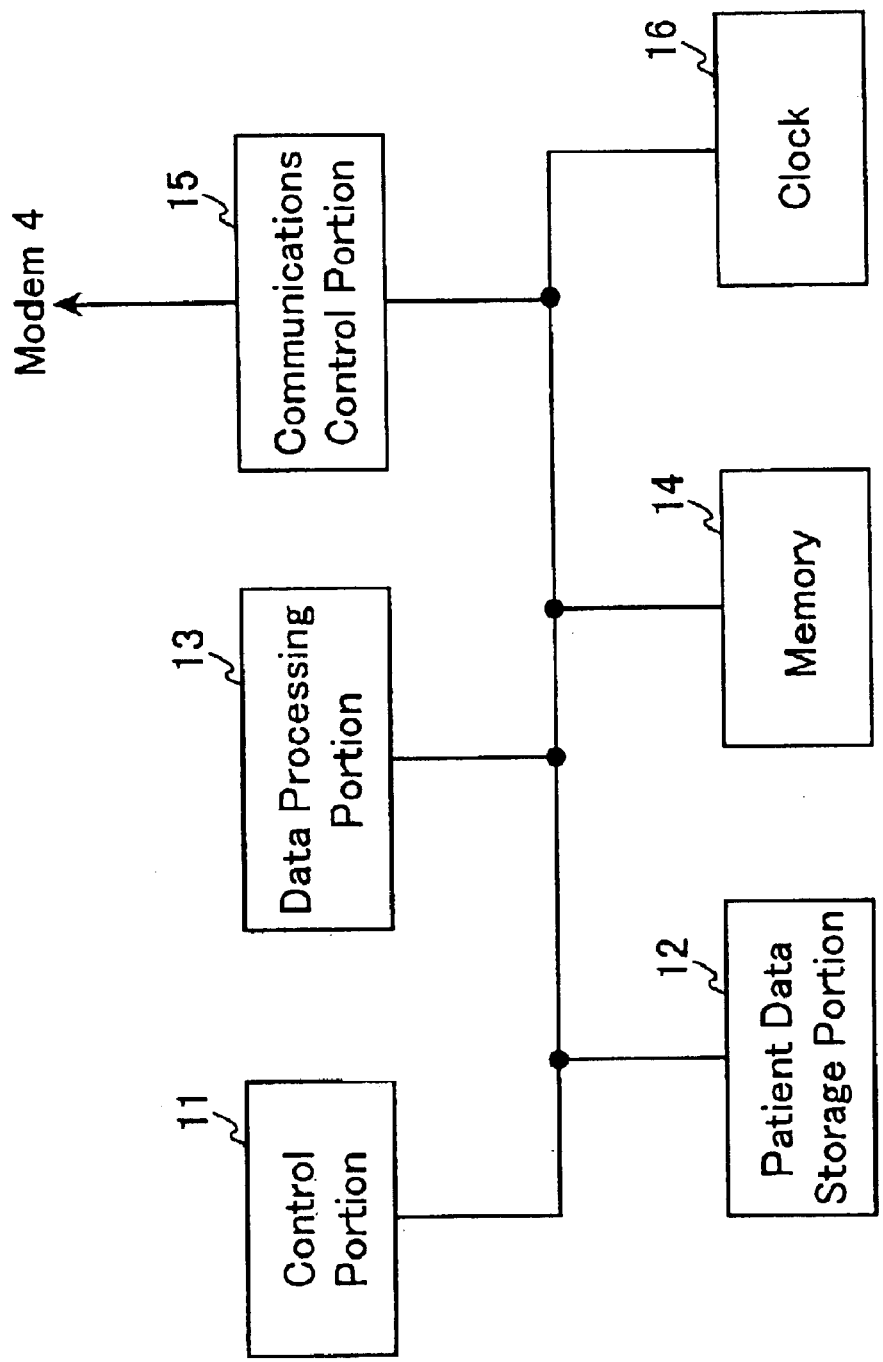
FIG. 4 is a block diagram showing the configuration of a server that is established in a medical institution in the remote health management system.

FIG. 4 is a block diagram showing the configuration of the server 1 of the medical institution A. As shown in FIG. 4, the server 1 is provided with a control portion 11 (control means), a patient data storage portion 12 (received data storage means), a data processing portion 13 (data processing means), a memory 14, a communications control portion 15, and a clock 16.

The control portion 11 is a CPU, for example, and is operated in accordance with a program so as to control the operation of each portion. The patient data storage portion 12, which is described in greater detail later, stores the measured data that are measured by each patient's personal measuring device 3 and the time that the data are measured, as well as the time at which the measured data are received by the server 1. The data processing portion 13 executes various processes, such as analyzing data transmitted from the patient. The memory 14 includes a function for temporarily storing data transmitted from the patients. The communications control portion 15 sends and receives data to and from the communications device 2 via the modem 4.

It should be noted that here, the patient data storage portion 12 illustratively is shown installed in the server 1, but the patient data storage portion 12 also can be provided in an outside memory device that can be accessed from the server 1.

Figure 5:
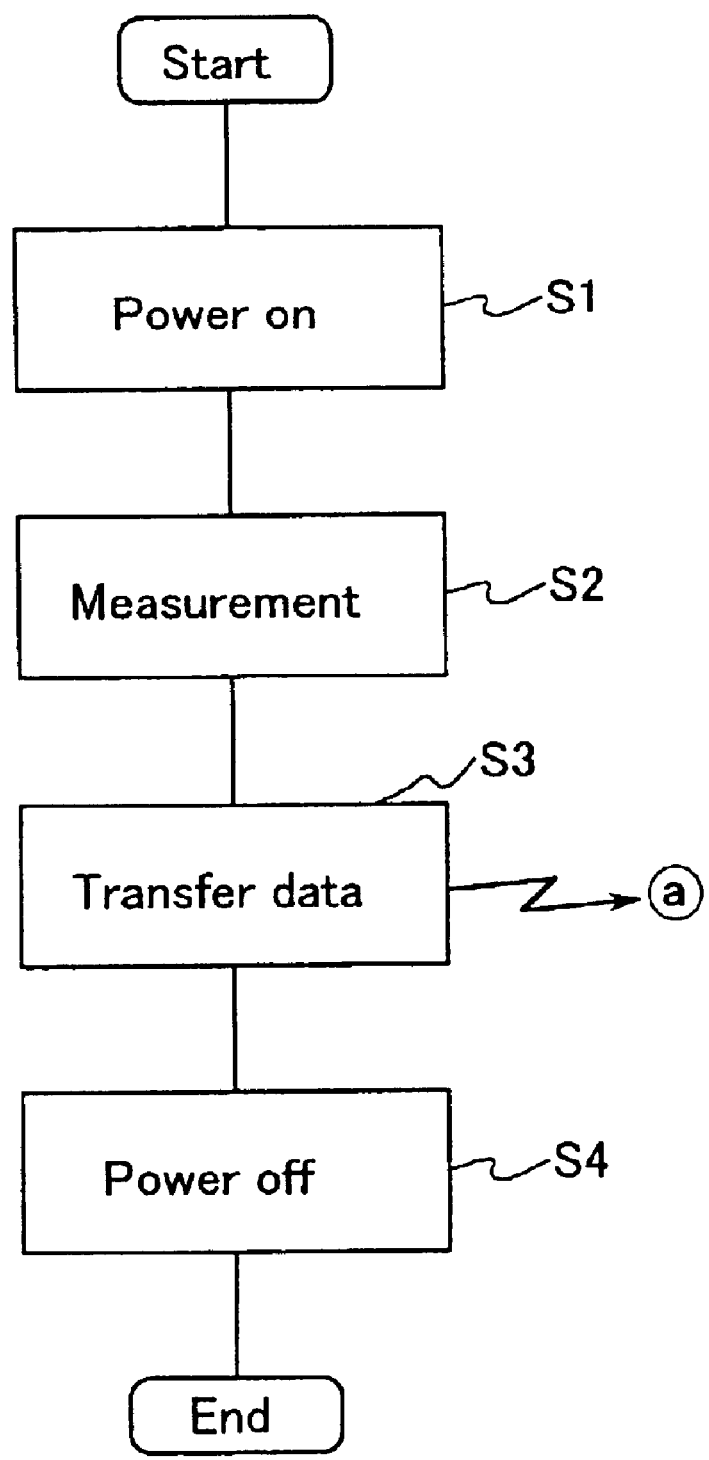
FIG. 5 is a flowchart showing the operation of the personal measuring device.
Figure 6:
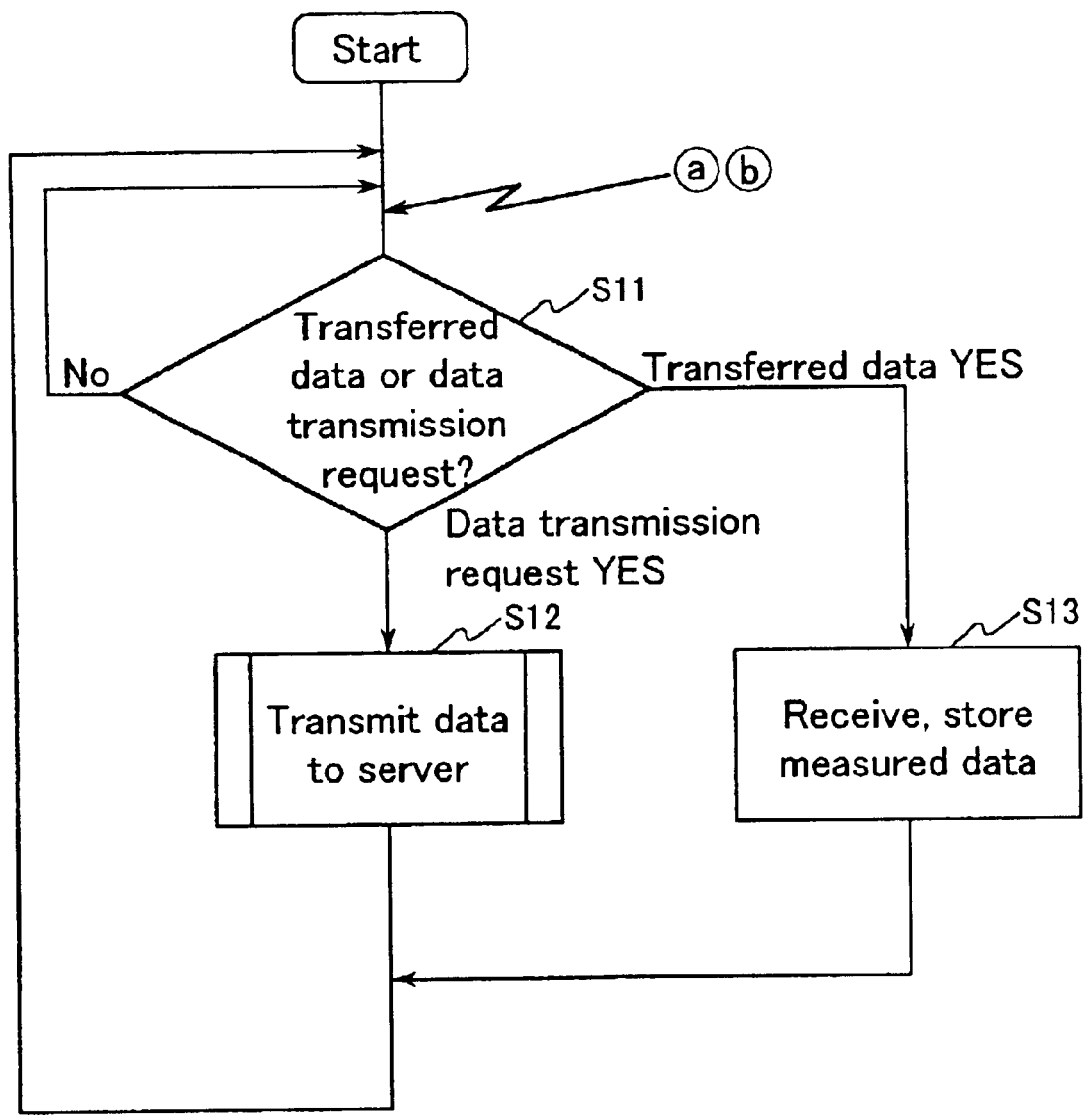
FIG. 6 is a flowchart showing the operation of the communications device.
Figure 7:
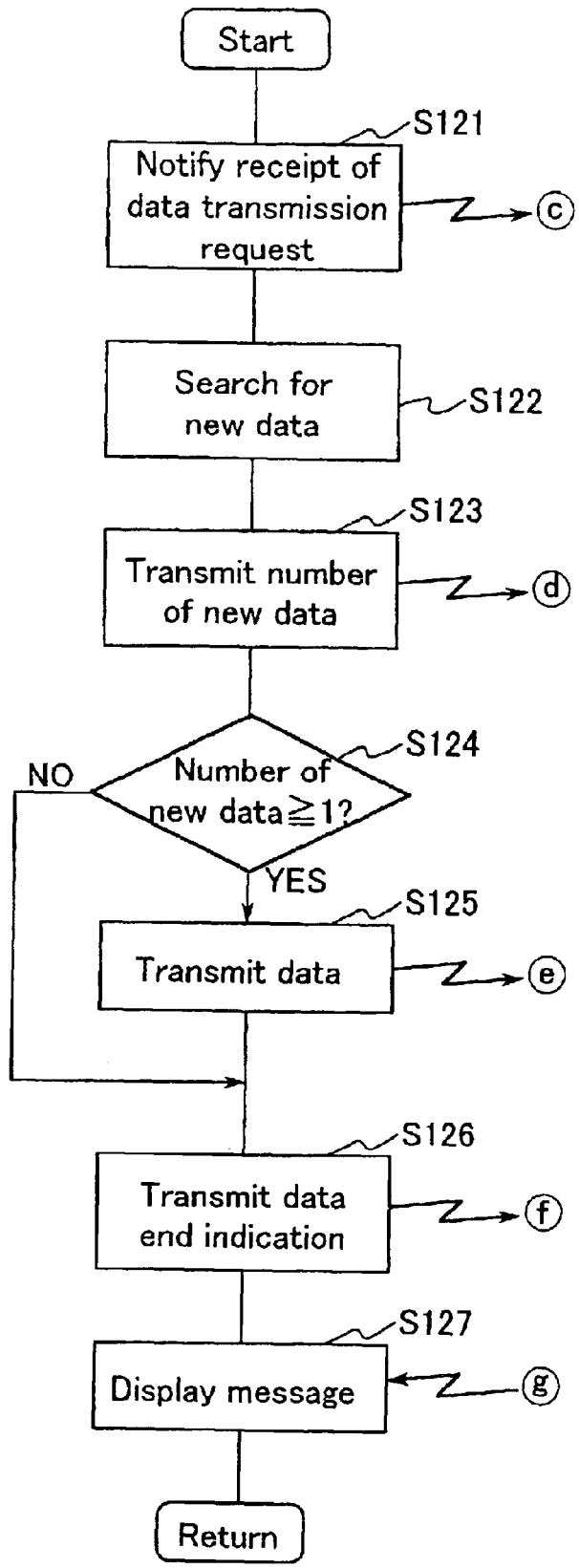
FIG. 7 is a flowchart showing the process of step S12 of FIG. 6 in detail.
Figure 8:
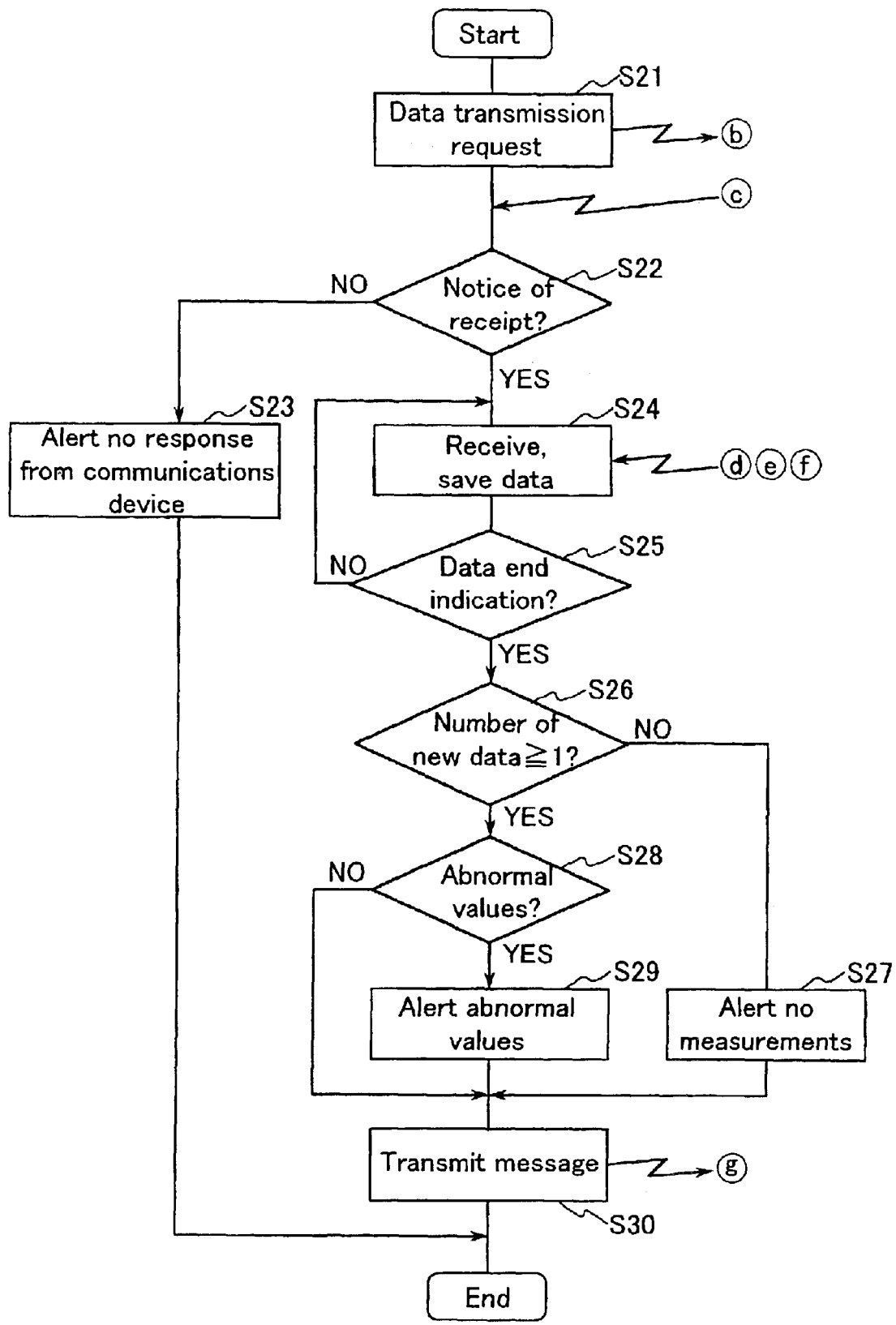
FIG. 8 is a flowchart showing the operation of the server.

Hereinafter, the operation of the remote health management system is described using FIGS. 5 to 8. FIG. 5 is a flowchart showing the operation of the personal measuring device 3. FIGS. 6 and 7 are flowcharts showing the operation of the communications device 2. FIG. 8 is a flowchart showing the operation of the server 1. It should be noted that a blood glucose level meter serves as the personal measuring device 3 in the description of this embodiment, but the personal measuring device 3 of course is not limited to a blood glucose level meter.

First, the operation of the personal measuring device 3 and the communications device 2 when the patient uses the personal measuring device 3 (blood glucose level meter) to measure his blood glucose level is described. The patient measures his blood glucose level four times a day (before or after breakfast, lunch, and dinner, and before going to sleep).

As shown in FIG. 5, first the patient turns on the power of the personal measuring device 3 (step S1).

Then, the patient sets a disposable sensor in the personal measuring device 3, draws a small amount of blood by pricking his fingertip with a needle, and places a drop of blood onto the sensor set in the personal measuring device 3.

The measuring portion 31 of the personal measuring device 3 automatically recognizes that a drop of blood has been placed onto the sensor, and after a predetermined amount of time has passed after the drop of blood is placed, the measuring portion 31 obtains the output from the sensor. The sensor output that is obtained by the measurement portion 31 is converted into a blood glucose level by the conversion portion 32 and stored in the memory 33 as measured data (step S2). At this time, in correlation with the measured data, information on the data measurement time is acquired from the clock 34 and stored in the memory 33.

When measurement has ended, the patient connects the personal measuring device 3 to the communications device 2 via the cable. Consequently, the control portion 35 of the personal measuring device 3 retrieves the measured data and the data measurement time from the memory 33, retrieves the patient ID number, the device ID number, and the reagent information, for example, from the device information holding portion 37, and forwards these to the communications device 2 via the communications portion 36 (step S3). When transmission is over, the patient turns off the power of the personal measuring device 3 (step S4).

Thus, the power of the personal measuring device 3 is turned on and off by the patient for each measurement, that is, four times a day. In contrast, the communications device 2 is always on standby and capable of communication, and thus the power is always on. As shown in FIG. 6, the control portion 24 detects that there has been (a) a transfer of data from the personal measuring device 3 or (b) a data transmission request from the server 1 (step S11), and starts the following process.

As mentioned above, when measured values have been transferred from the personal measuring device 3 (data transmission), the control portion 24 of the communications device 2 advances the procedure to the control of step S13, and stores the data that have been forwarded from the personal measuring device 3 into the memory 22 (step S13). When the process of step 13 has ended, the control portion 24 of the communications device 2 returns the procedure to the control of step S11.

As set forth above, each time the patient uses the personal measuring device 3 to carry out a measurement, the blood glucose level that is measured is transmitted to and stored in the memory 22 of the communications device 2 along with the measurement time, the patient ID number, the device ID number, and the reagent information, for example.

On the other hand, the server 1 of the medical institution A periodically accesses each patient's communication device 2 and gathers the measured data, for example, of the patients. The access frequency is set in advance to daily, biweekly, or monthly, for example. As mentioned previously, the measured data for each patient and the time when the server 1 received those data are stored in the patient data storage portion 12 of the server 1. Consequently, the control portion 11 of the server 1 acquires the most recent data reception time for each patient from the patient data storage portion 12, and when a predetermined period of time corresponding to the access frequency has passed from this data reception time, connects to the communications device 2 of that patient via the modem 4 and the public communications network 10 using the communications control portion 15 and transmits a data transmission request (step S21 in FIG. 8).

As shown in FIG. 6, when the communications device 2 of patients to which a data transmission request has been transmitted detects that there has been a data transmission request, the control portion 24 advances the procedure to the control of step S21 and transmits data to the server 1. The process of step S12 is detailed below with reference to FIGS. 7 and 8.

First, the control portion 24 of the communications device 2 notifies the server 1, via the telephony device 23, that it has received the data transmission request (step S21 in FIG. 7). At the server 1, the control portion 11 determines, after a certain period of time has passed from transmission of the data transmission request, whether there has been a notification from the communications device 2 that the data transmission request has been received (step S22 in FIG. 8). If there has been a notification (YES in step S22), the process is continued from step S24, and if there has not been a notification (NO in step S22), then a warning that there has been no response from the communications device 2 is output and the process is ended.

At the communications device 2, after receipt of the data transmission request has been notified as mentioned above, the control portion 24 references the memory 22 and searches for data (new data) that have not yet been transmitted to the server 1 (step S122 in FIG. 7), and transmits the number of new data sets to the server 1 using the telephony device 23 (step S123).

If there are new data (YES in step S124), then those data are retrieved from the memory 22 and transmitted to the server 1 (step S125). It should be noted that the data transmitted in step S125 include the measured blood glucose level, the time of measurement, the patient ID number, the device ID number, and the reagent information. When transmission has ended, the control portion 24 transmits a data end symbol via the telephony device 23 (step S126).

The server 1 receives the various data that are transmitted from the communications device 2 and holds them until the data end symbol is transmitted from the communications device 2 (steps S24 and S25 in FIG. 8). The various types of data that are transmitted from the communications device 2 during this period include the number of new data sets transmitted in step S123, and when there are new data, the data that are transmitted in step S125 (e.g. blood glucose level, time of measurement, patient ID number, device ID number, and reagent information).

Next, the server 1 analyses the data that are transmitted from the communications device 2 using the data processing portion 13, and by determining whether the number of new data sets is one or more, it determines whether there are data that have been newly measured since data were last gathered from the communications device 2 of that patient (step S26).

If there are no new data (NO in step S26), then the patient has not performed a measurement, and thus a message reading "Please make periodic measurements" is created (step S27).

If there are new data (YES in step S26), then the data processing portion 13 determines whether the blood glucose levels included in these new data fall within the normal range. If there are abnormal blood glucose levels (YES in step S28), then depending on the extent of disparity from the normal range, a message reading "Please work harder to control your blood glucose level" or a message reading "See your physician immediately" is created (step S29). If the level is not abnormal (NO in step S28), then a message reading "Excellent" may be created.

Next, the message created in step S27 or step S29 is transmitted to the communications device 2 of the patient by the communications control portion 15 (step S30), and the control portion 11 of the server 1 ends the process.

On the other hand, the communications device 2 of the patient receives the message that is transmitted from the server 1 in step S30 and displays this message on the display portion 25 (step S127 in FIG. 7), and the process is ended.

In the foregoing, with the present remote health diagnosis system, every time a patient uses his personal measuring device 3 to perform a measurement, the measured data are forwarded to the communications device 2 and stored, and the server 1 of the medical institution A sends a data transmission request to the communications device 2 of each patient so as to control the timing at which data are transmitted by the communications device 2.

Thus, the problem of connections to the server being concentrated at particular times, which is the case with conventional systems in which data are transmitted from the patient to the server each time a measurement is made, does not occur. Thus there is the advantage that medical institutions do not have to make equipment investments such as increasing the number of lines that connect to the server from the outside. Additionally, patients can be spared the work of carrying out data transmissions after each measurement.

It should be noted that the present invention is not limited to the foregoing embodiment. For example, in the above description, a telephone network served as an example of the communications network, but other possibilities include the use of a CATV network or a dedicated line. Also, the personal measuring device is not limited to a blood glucose level meter, and a variety of other measuring devices including electrocardiograms, sphygmomanometers, scales, and urine analysis devices also can be used. Moreover, the data management device was illustratively described as a server connected to a LAN within the medical institution, but is not limited to a server, and also can be a host computer or a personal computer, for example.

In the above embodiment, the measuring system was configured by connecting the personal measuring device 3 and the communications device 2 with a cable or the like, but this connection is not limited to a wired connection, and also can be a wireless connection such as infrared light.

Additionally, the measuring system can be achieved through a single device that includes the functions of both the personal measuring device 3 and the communications device 2.

INDUSTRIAL APPLICABILITY

As described above, according to the present invention, the transmission of measured data from the measuring devices of managed persons, such as patients, to a data management device is controlled on the data management device side so that the transmissions are not concentrated at particular times, and thus a remote data management system with which data can be gathered efficiently and which requires a minimum equipment investment can be provided.

What is claimed is:

1. A remote data management system comprising a measuring device with which a managed person can perform a measurement of data and a data management device for managing measured data of each managed person that are obtained with the measuring device, wherein the measured data obtained with the measuring device are collected to and managed by the data management device via a communications network, the remote data management system further comprising:

a communications device that communicates with the measuring device, having a measured data storage means for storing measured data obtained by the measuring device and a data transmission means for transmitting the measured data to the communications network, wherein, when communicating with the measuring device, the communications device receives measured data from the measuring device and stores the measured data in the measured data storage means, and when a transmission request for the measured data is received from the data management device, the communications device reads out the measured data stored in the measured data storage means and transmits the measured data to the data management device via the communications network using the data transmission means; and a control means for controlling the timing at which the data management device connects to the communications device of each managed person via the communications network and performs a transmission request for the measured data, wherein the data management device comprises a received data storage means for storing received measured data together with a time of reception for each managed person, and the control means determines the timing at which to carry out the transmission request to the communications device of each managed person based on a most recent time of reception of the measured data stored in the received data storage means for that managed person.

2. The remote data management system according to claim 1, wherein the measured data that are managed by the data management device are data related to managing the health of the managed persons.

3. The remote data management system according to claim 1, wherein the data management device comprises a data processing means for analyzing measured data that have been received, and the results of the analysis by the data processing means are transmitted to the communications device.

4. The remote data management system according to claim 3, wherein the data processing means creates a message for alerting a managed person to perform periodic measurements and includes this message in the results of the analysis, when a number of measured data sets that are measured after previous measured data of that managed person have been received is lower than a number of measurements that should have been performed.

5. The remote data management system according to claim 1, wherein the control means of the data management device adjusts the timing at which transmission requests are sent to the communications device of each managed person, so that transmission of measured data from managed persons is spread out so that it is not concentrated at particular times.

6. The remote data management system according to claim 1, wherein the communications network is a telephone network and the communications device is a mobile communications type telephony device.

7. The remote data management system according to claim 1, wherein the measuring device is a blood glucose level meter.

8. The remote data management system according to claim 1, wherein the measuring device and the communications device are configured as a single device.

9. A remote data management system comprising a measuring device with which a managed person can perform a measurement of data and a data management device for managing measured data of each managed person that are obtained with the measuring device, wherein the measured data obtained with the measuring device are collected to and managed by the data management device via a communications network, the remote data management system further comprising:
   a communications device that communicates with the measuring device, having a measured data storage means for storing measured data obtained by the measuring device and a data transmission means for transmitting the measured data to the communications network, wherein, when communicating with the measuring device, the communications device receives measured data from the measuring device and stores the measured data in the measured data storage means, and when a transmission request for the measured data is received from the data management device, the communications device reads out the measured data stored in the measured data storage means and transmits the measured data to the data management device via the communications network using the data transmission means: and
   a control means for controlling the timing at which the data management device connects to the communications device of each managed person via the communications network and performs a transmission request for the measured data,
   wherein, when the communications device receives the data transmission request from the data management device, the communications device retrieves from the measured data storage means only measured data that have not yet been transmitted to the data management device, and transmits them to the data management device.

10. A measurement system wherein data measured by a measuring device with which a managed person measures data are transmitted, via a communications network, from the measuring device to a data management device for managing the measured data of the managed person, the measurement system comprising:
   a communications device having a measured data storage means for storing measured data obtained with the measuring device and a data transmission means for transmitting the measured data over the communications network, wherein, when connected to the measuring device, the communications device receives measured data from the measuring device and stores the measured data in the measured data storage means, and when a transmission request for the measured data is received from the data management device, the communications device reads out the measured data stored in the measured data storage means and transmits the measured data to the data management device over the communications network using the data transmission means,
   wherein, when the communications device receives the transmission request for the measured data from the data management device, the communications device retrieves from the measured data storage means only measured data that have not yet been transmitted to the data management device, and transmits them to the data management device using the data transmission means.

11. The measurement system according to claim 10, wherein the measuring device and the communications device are configured as a single device.

12. The measurement system according to claim 10, wherein the communications network is a telephone network and the communications device is a mobile communications type telephony device.

13. The measurement system according to claim 10, wherein the measuring device is a blood glucose level meter.

14. A method for gathering measured data, wherein
   in a remote data management system including a measuring device with which managed persons can perform a measurement of data, a data management device for managing measured data of each managed person obtained with the measuring device, and a communications device that is connected to the measuring device and used by the managed persons, wherein the communications device has a measured data storage means for storing the measured data and transmits the measured data to the data management device via a communications network,
   the measured data of the managed persons obtained with the measuring device are gathered in the data management device; the measured data gathering method comprising
   connecting the measuring device to the communications device and storing the measured data obtained with the measuring device in the measured data storage means of the communications device;
   connecting the data management device to the communications device of the each managed person via the communications network at a predetermined timing and performing a transmission request for the measured data; and
   the communications device reading out the measured data from the measured data storage means and transmitting the measured data to the data management device via the communications network when the transmission request for the measured data is received from the data management device,
   wherein the timing at which the data management device carries out the transmission request for measured data to the communications device of each managed person is determined based on a last time the measured data for that managed person was received.

15. A communications device in a remote data management system including a measuring device with which managed persons can perform a measurement of data, and a data management device for managing measured data for managed persons obtained with the measuring device, wherein the communications device communicates with the measuring device, and is connected to the data management device via a communications network and transmits measured data that are received from the measuring device to the data management device, the communications device comprising:
- a measured data storage means for storing measured data obtained with the measuring device; and
- a data transmission means for transmitting the measured data over the communications network;
- wherein, when communicating with the measuring device, the communications device receives measured data from the measuring device and stores the measured data in the measured data storage means, and when a transmission request for the measured data is received from the data management device, the communications device reads out the measured data stored in the measured data storage means and transmits the measured data to the data management device over the communications network using the data transmission means, and
- when the communications device receives the transmission request for the measured data from the data management device, the communications device retrieves from the measured data storage means only measured data that have not yet been transmitted to the data management device, and transmits them to the data management device using the data transmission means.

16. The communications device according to claim 15, wherein the communications network is a telephone network and the communications device is a mobile communications type telephony device.

17. A method for gathering measured data, wherein
in a remote data management system including a measuring device with which managed persons can perform a measurement of data, a data management device for managing measured data of each managed person obtained with the measuring device, and a communications device that is connected to the measuring device and used by the managed persons, wherein the communications device has a measured data storage means for storing the measured data and transmits the measured data to the data management device via a communications network,
the measured data of the managed persons obtained with the measuring device are gathered in the data management device; the measured data gathering method comprising
connecting the measuring device to the communications device and storing the measured data obtained with the measuring device in the measured data storage means of the communications device;
connecting the data management device to the communications device of the each managed person via the communications network at a predetermined timing and performing a transmission request for the measured data; and
the communications device reading out the measured data from the measured data storage means and transmitting the measured data to the data management device via the communications network when the transmission request for the measured data is received from the data management device,
wherein, when the transmission request for the measured data is received from the data management device, only measured data from among the measured data stored in the measured data storage means that have not yet been transmitted to the data management device are retrieved, and only the measured data that are retrieved are transmitted to the data management device.

18. A program storage medium, on which is stored a program for controlling operation of a communications device in a remote data management system that includes a measuring device with which managed persons can perform a measurement of data and a data management device for managing the measured data of each managed persons that are obtained with the measuring device, wherein the communications device communicates with the memory device and is connected to the data management device via a communications network and transmits the measured data that are received from the measuring device to the data management device;
- wherein the program executes on the communications device:
- a storage process for receiving measured data from the measuring device and storing the measured data in a storage means; and
- a transmission process for reading out only measured data from among the measured data stored in the storage means that have not yet been transmitted to the data management device and transmitting the measured data to the data management device via the communications network when the transmission request for the measured data is received from the data management device.

19. A data management device, which receives via a communications network measured data from a measurement system including a measuring means with which a managed person can perform a measurement of data, a measured data storage means for storing the measured data obtained by the measuring means, and a data transmission means for reading out the measured data from the measured data storage means when a transmission request for the measured data is received via a communications network, and manages the measured data, the data management device comprising:
- a control means that is connected to the measuring system of each managed person via the communications network and controls the timing at which the transmission request for the measured data is performed; and
- a received data storage means for storing measured data received from the measuring system together with a time of reception for each managed person,
- wherein the control means determines the timing at which to carry out the transmission request to the measuring system of each managed person based on a most recent time of reception of the measured data stored in the received data storage means for that managed person.

20. The data management device according to claim 19, further comprising a data processing means for analyzing measured data that are received from the measuring system, wherein the data management device transmits results of the analysis by the data processing means to the measuring system using the communications means.

21. The data management device according to claim 20, wherein the data processing means incorporates, into the results of the analysis, a message alerting a managed person to perform periodic measurements, when, of the measured data that are received from the measuring system, a number of measured data sets that are measured after previously measured data of that managed person are received is less than a number of measurements that should have been performed.

22. A program storage medium on which is stored a program for controlling operation of a data management device that receives and manages measured data of managed persons via a communications network from a measurement system including a measuring means with which the managed persons can perform a measurement of data, a storage means for storing measured data obtained with the measuring means, and a data transmission means for reading out the measured data from the storage means and transmitting the measured data over the communications network when a request for transmission of the measured data is received via the communications network, wherein the data management device is provided with a received data storage means for storing the measured data of each managed person that are received and a time of reception thereof;

wherein the program executes on the data management device a procedure with which the data management device:

determines a timing at which the request for transmission of the measured data should be sent to the measuring system of each managed person based on a most recent time of reception of the measured data stored in the received data storage means for that managed person; and connects to the measuring system of each managed person via the communications network at the determined timing and performs the request for transmission of the measured data.

\* \* \* \* \*